United States Patent [19]
Quinn et al.

[11] Patent Number: 5,556,445
[45] Date of Patent: Sep. 17, 1996

[54] STEAM TREATMENT OF MUNICIPAL SOLID WASTE

[75] Inventors: Mark K. Quinn, 210 Baronne St., New Orleans, La. 70112; Bruce E. Unangst, Slidell, La.

[73] Assignee: Mark K. Quinn, New Orleans, La.

[21] Appl. No.: 310,574

[22] Filed: Sep. 22, 1994

Related U.S. Application Data

[63] Continuation of Ser. No. 996,132, Feb. 23, 1993, abandoned, which is a continuation of Ser. No. 681,765, Apr. 8, 1991, abandoned.

[51] Int. Cl.$^6$ .................... B09B 3/00; A61L 11/00
[52] U.S. Cl. .................... 71/11; 71/14; 71/901; 422/26; 422/209; 209/11; 209/238; 209/240; 209/284; 209/288; 209/930
[58] Field of Search .................... 71/8–14, 901; 210/770, 771, 774, 808, 784; 422/26, 209; 209/11, 238, 240, 284, 288, 930

[56] References Cited

U.S. PATENT DOCUMENTS

| | | | |
|---|---|---|---|
| 742,226 | 10/1903 | Peck et al. | 71/14 |
| 1,617,014 | 2/1927 | Derleth | 71/9 |
| 1,938,647 | 12/1933 | Earp-Thomas | 71/14 |
| 2,317,992 | 5/1943 | Grether | 71/10 |
| 2,723,954 | 11/1955 | Young | 71/12 |
| 2,823,106 | 2/1958 | Pierson | 71/9 |
| 2,969,277 | 1/1961 | Carlsson | 71/901 |
| 3,055,744 | 9/1963 | Petersen | 71/9 |
| 3,235,369 | 2/1966 | Eweson | 71/22 |
| 3,236,604 | 2/1966 | Pierson | 71/9 |
| 3,272,740 | 9/1966 | Gitchel et al. | 71/9 |
| 3,359,200 | 12/1967 | Gitchel et al. | 71/12 |
| 3,365,395 | 1/1968 | McDonald | 71/12 |
| 3,451,800 | 6/1969 | Hudson et al. | 71/12 |
| 3,932,166 | 1/1976 | Vignovich et al. | 71/11 |
| 4,010,098 | 3/1977 | Fassell | 71/12 |
| 4,056,380 | 11/1977 | Thiac | 71/9 |
| 4,079,837 | 3/1978 | Grube et al. | 71/901 |
| 4,342,830 | 8/1982 | Holloway | 71/14 |
| 4,483,704 | 11/1984 | Easter, II | 71/9 |
| 4,540,467 | 9/1985 | Grube et al. | 71/64.03 |
| 4,540,495 | 9/1985 | Holloway | 210/774 |
| 4,769,149 | 9/1988 | Nobilet et al. | 71/10 |
| 4,971,616 | 11/1990 | Glogowski | 71/9 |
| 4,983,296 | 1/1991 | McMahon et al. | 210/774 |

OTHER PUBLICATIONS

*Composting, a Study of the Process and its Principles* by Clarence G. Golueke, Ph.D., Research & Biologist, Sanitary Engineering Research Laboratory, University of California, Berkely Rodale Press, Inc.

Primary Examiner—Robert J. Popovics
Attorney, Agent, or Firm—David L. Ray

[57] ABSTRACT

A method for treating solid municipal waste material including placing solid municipal waste in a rotating chamber having an interior at ambient pressure, heating the waste at ambient pressure, and controlling the moisture content of the waste.

1 Claim, 1 Drawing Sheet

STEAM TREATMENT OF MUNICIPAL SOLID WASTE

This is a continuation of application Ser. No. 07/996,132 filed Feb. 23, 1993, now abandoned, which was a continuation of application Ser. No. 07/681,765 filed Apr. 8, 1991, now abandoned.

BACKGROUND OF THE INVENTION

1. Field of the Invention

The present invention is related to treatment of municipal waste to recover useful organic products, ferrous and non-ferrous metals, plastic products, or other recyclable materials therefrom. In particular, the present invention is related to the treatment of municipal solid waste with steam to promote conversion of organic products such as paper and food waste contained in the waste, and to provide for the recovery of recyclable and useable fractions of the treated waste for beneficial use.

2. Description of the Related Art

Processes for treating municipal waste are known in the art. Exemplary of the processes for treating waste materials are the following U.S. Patents:

U.S. Pat. No. 4,983,296 discloses a method of partial oxidation of sewage sludge whereby municipal sanitary sewage sludge is disposed of by an improved partial oxidation process without polluting the environment. Aqueous slurries of sewage sludge are upgraded by hydrothermal treatment, preferably while being sheared, concentrated, and then mixed with a supplemental fuel, preferably coal. A pumpable aqueous slurry of sewage sludge-coat and/or petroleum coke is thereby produced having a greater total solids and heat content (HHV) as well as containing an increased amount of sewage sludge for reacting with free-oxygen containing gas in a free-flow partial oxidation gas generator. Hot quench water or steam produced by cooling the raw effluent stream of synthesis gas, reducing gas or fuel gas from the gasifier may provide heat for the hydrothermal step.

U.S. Pat. No. 4,971,616 discloses a process for converting municipal garbage into organic compost material. In the first step of this process, a mixture of shredded cellulosic refuse material and earthworms is provided. A substantial portion of the shredded cellulosic refuse materials derived from paper and/or cardboard refuse. In the second step of the process, the mixture of refuse material and earthworms is maintained at a moisture content of from about 45 to about 92 weight percent and a temperature of from about 0 to about 54 degrees centigrade for from about 4 to about 8 months.

U.S. Pat. No. 4,769,149 discloses a process for recovery of energy from waste and residues. The residues, after sieving, are subjected to bacterial digestion in a methanization reactor and the solid phase of the digestate is then subjected to incineration in a furnace supplying a heat recuperator, the furnace being supplied with complementary combustible by the methane coming from the digester, while the circuit of the fumes downstream of the recuperator is used for heating by at least one secondary circuit, the magma in the course of treatment in the digester and/or the sludge separated from the digestate before recycling thereof towards the digester.

U.S. Pat. No. 4,540,495 discloses a process for treating municipal solid waste material in the presence of moisture for the separation and recovery of inorganic matter and organic matter wherein the waste material is fed into a pressure chamber and is agitated therein. The contents of the pressure chamber are subjected to heat under a pressure for a predetermined period of time to cook, sterilize and soften the organic matter contained therein. The moisture content of the waste material is controlled so that the fines of the organic fraction have a residual moisture content ranging from about 60% to 70%. After releasing the pressure from the pressure chamber, the cooked waste material is removed and then separated and classified into various fraction thereof including an inorganic fraction and the fines of the organic fraction having a residual moisture content ranging from approximately 60% to 70%.

U.S. Pat. No. 4,540,467 discloses a method and apparatus for the removal of mold core material from metal castings and for fragmentation of municipal waste material, e.g. paper products, involving heating and hydrating the materials within a pressure vessel. Chemicals active on the material to be processed or the hydration water are added during hydration to soften the material to be removed or fragmented. Excess liquid in the vessel is drained and pressurized steam is added for a selected period of time. A suitable temperature and pressure are achieved such that the moisture or liquid carried by the processed material will rapidly turn to steam or vapor when the pressure in the vessel is rapidly reduced by quickly opening an unloading means at the bottom of the pressure vessel. The sudden release of the pressure in the vessel causes the moisture to change to steam and a certain portion of the liquid in the material to flash to vapor in accordance with thermodynamic laws. The resulting rapid expansion within the processed material fragments it.

U.S. Pat. No. 4,342,830 discloses a process for recovering organics and inorganics from waste material with a specific object of preparing the separated organic fraction for the production of ethanol wherein rigid organic matter becomes soft when subjected to heat and pressure. The process is carried out by first, feeding the waste material into a perforated container mounted within a closed chamber. Next, the waste material is agitated and subjected to heat and pressure which sterilizes it and softens the organics contained therein. After heating under pressure, the pressure is suddenly released from the chamber which forces the softened organics outwardly of the container, thus separating them from the inorganics for further processing to recover fuels and animal feed supplements.

U.S. Pat. No. 4,079,837 discloses a system for the separation of fragmented solid waste which has been treated by thermal explosive decomposition followed by biodegradation (also hereinafter referred to as composting) is presented. The explosive decompression and composting pretreatment before separation presents a granular and inoffensive finely-divided product mixed with less-fragmented non-biodegradable materials such as plastic, metals ad other substances. The method first separates the finely-divided product from the waste to leave a first residue, then magnetically separates any magnetic components from the first residue to leave a second residue, and then separates by gravity flotation any plastic components from the second residue, each step being carried out successively without interruption for further treatment of the waste. A system is described which separates the biodegradable and fine residues first, followed by the separation of other, more valuable components from each other at later stages of separation.

U.S. Pat. No. 4,056,380 discloses a method of producing an organic soil additive and the product thereof. The present disclosure is directed to a method of producing an organic soil additive from shredded water hyacinths and a mixture of secondary sewage combined in spaced apart heaps for aeration and composting with subsequent steam treatment to produce a product having high moisture retention characteristics for use as a soil additive, conditioner, amendment, fertilizer ingredient and/or agent or potting soil.

U.S. Pat. No. 4,010,098 discloses a method for treatment of solid waste and sewage sludge with the recovery of natural resources comprising subjecting all or at least a portion of the sewage sludge to wet oxidation reaction to reduce the COD by an amount of at least 50% and preferable 50–85% and using the excess heat from the wet oxidation reaction to dry the solid waste and subjecting the combined solids from the wet oxidation reaction and the solid waste to pyrolysis under non-oxidizing conditions whereby the products from the pyrolysis reaction are readily separable into valuable constituents which are easily recoverable.

U.S. Pat. No. 3,932,166 discloses a method for converting organic waste materials into inert humus-like materials by charring the organic waste materials by heating and drying same in the presence of certain water-soluble inorganic acids, removing residual acid and other water-soluble contaminants by washing the crude char product with water and utilizing the resulting inert material as a landfill. If desired, the humus-like char products can be reacted with an alkali at elevated temperatures, and the resulting alkali salts of humic-acid-like materials can be mixed with the soil to provide an improved and/or fertilized topsoil.

U.S. Pat. No. 3,365,395 discloses a process for treating sewage with a halogenated hydrocarbon solvent. In the art of converting raw sewage to a sterile fertilizer, the method comprising the steps of grinding said raw sewage in contact with a halogenated hydrocarbon solvent which has azeotrophy with water to form a sludge and effluent mixture, separating the sludge from the effluent by stratification and decantation, dehydrating the sludge by heating it while in contact with the halogenated hydrocarbon solvent, and vaporizing the solvent from the dehydrated sludge.

U.S. Pat. No. 3,451,800 discloses a method of production of granular sewage sludge. Sewage sludge which contains woolly fiber distributed therethrough is ground until 95 percent of the material will pass a 50-mesh screen, and to the ground material is added about ½ to 1 percent of starch by weight, the mass being then heated by steam to a temperature of about 185°–200° F. while tumbling the mass to form granules and then drying the granular product. The dried sewage sludge granules are smooth and have rounded non-dusting exterior surfaces.

U.S. Pat. No. 3,359,200 discloses a method for partial wet air oxidation of sewage sludge. In a continuous process for the wet air partial oxidation of sewage sludge at a substantially constant temperature in which a continuous stream of said sludge of substantially constant volume is pre-heated by indirect countercurrent heat exchange with a continuous stream of the oxidized sludge and then partially oxidized at a temperature above 150° C. with a substantially constant volume of air in an amount sufficient to maintain gaseous oxygen in the oxidized mixture, the improvement which comprises (a) pre-heating a mixture of the sludge and air by the indirect heat exchange to a temperature not exceeding 150° C.; (b) heating the pre-heated sludge and air mixture to a temperature above 150° C. by injecting steam directly into the mixture; (c) maintaining the sludge at the selected temperature for a period of time which reduces from 5 to 45 percent the Chemical Oxygen Demand of the sludge by non-autogenetic wet air oxidation; and (d) maintaining the reaction temperature substantially constant by varying the amount of steam injected into the sludge in response to variations in the reaction temperature.

U.S. Pat. No. 3,272,740 discloses a sewage sludge treatment process which is a continuous process for producing from sewage sludge innocuous, substantially color-free, cured organic sludge having optimum processing characteristics which comprises the steps of (a) continuously mixing a substantially constant volume of sewage sludge with a substantially constant volume of air in a selected proportion which supplies to the mixture an amount of gaseous oxygen capable of reducing by more than 5 percent the C.O.D. of the sludge by oxidation, to produce a mixture having a gaseous and a liquid phase; (b) continuously heating a stream of the resultant mixture to a temperature above about 170° C. under conditions capable of consuming all the oxygen in the mixture; (c) heating the mixture for a period of time which reduces the C.O.D. of the sludge by between 5 percent and 45 percent and which maintains between about 0.5 percent and 6.5 percent gaseous oxygen content in the gaseous phase of the oxidized mixture, thereby producing a cured innocuous fibrous sludge having lower specific resistance to filtration and a higher settling rate and whose insoluble solids have lower water holding capacity, compared with the starting sludge; (d) continuously separating the gaseous phase from the liquid phase of the oxidized mixture; and (e) maintaining substantially constant the amount of gaseous oxygen consumed by adjusting the temperature to which the mixture is heated in a manner which is directly proportional to variations from the average in the gaseous oxygen content of the gaseous phase obtained from the oxidation, thereby maintaining the sludge at all times in the presence of gaseous oxygen during the wet air oxidation.

U.S. Pat. No. 2,317,992 discloses a method of treating proteinic material to produce a plant stimulant, plant nutrients and to cause an increase in the bacterial count within the mass, which comprises subjecting proteinic material to fermentation under substantially anaerobic conditions at temperatures between 15° and 40° C. in the presence of a water-soluble iron compound, an alkali base in amount sufficient to give he mixture a pH value between 7 and 9 and sufficient water to form a paste of the mixture.

U.S. Pat. No. 1,938,647 discloses a method of producing an inoffensive organic end-product from putrifiable organic waste material which comprises inoculating said material with thermophile aerobic bacteria to effect its bacterial decomposition, aerating and agitating said material and controlling its temperature during said decomposition, and drying the product thus obtained.

U.S. Pat. No. 1,617,014 discloses an improvement in activated sludge sewage disposal processes; consisting in introducing diatomaceous earth into the sewage prior to aeration thereof whereby nitrification and coagulation of the suspended solids in such sewage is accelerated; fats and oils are absorbed by the diatomaceous earth and the subsequent filtration of the sludge is facilitated.

U.S. Pat. No. 742,226 discloses a method of treating garbage. The improved subprocess for treating garbage which consists of expressing liquid from tankage, cooking such expressed liquid and raw garbage in a closed air-tight receptacle by radiated heat, and then separating from such receptacle vaporous and free-water content by exhausting both the normal vapors and also those that result from the water which is volatilizing.

SUMMARY OF THE INVENTION

In accordance with the present invention there is provided a method for treating solid municipal waste material including placing solid municipal waste in a rotating chamber having an interior at ambient pressure, heating the waste at ambient pressure, and controlling the moisture content of the waste.

The present invention has the advantage of providing a process for treating municipal waste without the use of a pressure vessel.

The present invention has the additional advantage of providing a continuous process for treating municipal waste to recover useful materials therefrom.

Furthermore, the present method has the advantage of being low in cost.

BRIEF DESCRIPTION OF THE DRAWINGS

The invention will be more easily understood by reference to the drawings in which.

DESCRIPTION OF THE PREFERRED EMBODIMENTS

Figure 1:
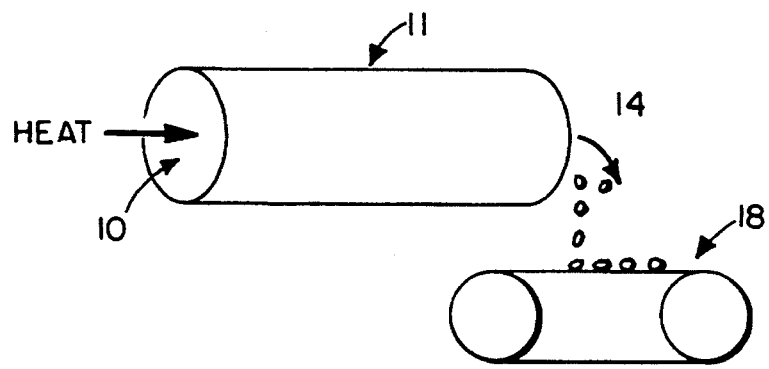
FIG. 1 shows a schematic diagram of the method of the invention.

Referring now to the drawings, and in particular to FIG. 1, the solid municipal waste material to be treated is fed into the entrance 10 of a rotatable chamber open or vented to the atmosphere or recaptured for use in adding moisture and heat to the waste materials, generally indicated by the numeral 11 and is agitated therein by rotating the chamber 11 by any conventional method known in the art. Chamber 11 may be vented to the atmosphere by any method known in the art such as providing a hole in the entrance 10 or exit 14 of rotatable chamber 11 to provide communication between the interior of the chamber 11 and the atmosphere. Vented steam can also be captured and utilized to preheat and add moisture to the waste materials prior to or during processing.

Preferably chamber 11 is generally cylindrical in shape and has fins or other conventional internal projections or paddles (not shown) for agitating the solid municipal waste as the waste is heated. The internal projections may be constructed as is known in the art to convey solid waste material from an entrance 12 at one end of the chamber 11 to an exit 14 at the other end of chamber 16 as is known in the art.

Figure 2:
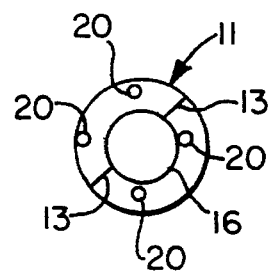
FIG. 2 shows a cross-sectional, schematic view of a preferred embodiment of the rotatable chamber of the invention.
Figure 3:
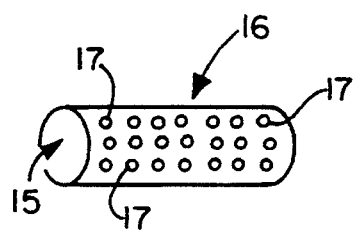
FIG. 3 shows a schematic side view of a perforated drum for attachment to the interior of the rotatable chamber of the invention.

In a preferred embodiment a perforated drum 16 shown in FIG. 3 is rigidly connected to the interior of rotatable chamber 11 as shown in FIG. 2 and solid waste material is loaded into the entrance 15 of perforated drum 16. The perforations 17 in perforated drum 16 are shown in FIG. 3. Perforated drum 16 may be connected to the interior of chamber 11 by struts 13—13 or by any other conventional method or structure.

As an alternative embodiment, the chamber 11 could be fixed and non-rotatable. The perforated drum 16 would rotate inside the fixed chamber. As the organic fraction of the waste material is pulped, these organic particles would pass through the perforations and be removed from the fixed chamber by a conveyor other mechanical devices known in the art.

After loading solid waste material into chamber 11 or perforated drum 16, preferably steam is injected into the chamber 11 through steam sparge lines 20 to heat the contents for a predetermined period of time to cook, sterilize and soften the organic matter contained therein. However, if desired, the contents of chamber 11 may be heated by conveying hot air to the interior of chamber 11, or by any other conventional method such as heating the surface of chamber 11 with flame provided by burning gas or solid fuel. Chamber 11 is vented to the atmosphere to prevent the pressure in chamber 11 from rising above ambient pressure.

The moisture content of the solid waste material is controlled so that the fines of the organic fraction have a residual moisture content ranging from about 35% to 70%. Moisture control can be accomplished by the addition of water directly into the chamber 11 or by moisture contained in steam added to chamber 11. The organic portion can be further dried by heating to provide a product suitable for use as a combustion fuel.

After heating the contents of the rotating chamber 11 for the desired amount of time, the treated waste material is removed and then separated and classified into various fractions thereof including an inorganic fraction and the fines of the organic fraction having a residual moisture content ranging from approximately 35% to 70%.

The separated organic fraction produced by the process of the invention disclosed above may be used to prepare a product high in fertilizer content which has physical properties similar to conventional garden products commonly referred to in the art as potting soil.

The contents of chamber 11 should preferably remain in the chamber 11 for about 10 minutes to about 90 minutes before they are discharged from the exit 14 of chamber 11.

When heat is supplied to chamber 11 by live steam, the steam introduced into rotating chamber 11 should preferably have an initial temperature ranging from about 212 degrees Fahrenheit(F.) to about 500 degrees F. and is continuously injected into the chamber. The contents of rotating chamber 11 are thus biologically sterilized and the organic matter, such as vegetable matter, bones meat scraps, paper and the like are softened and partially hydrolyzed.

When heat is supplied to chamber 11 by a heat source other than live steam, the rotating chamber 11 should preferably be heated to a temperature ranging from about 150 degrees Fahrenheit(F.) to about 500 degrees F. More preferably, rotating chamber 11 should preferably be heated to a temperature ranging from about 212 degrees Fahrenheit(F.) to about 500 degrees F. The contents of rotating chamber 11 are thus biologically sterilized and the organic matter, such as vegetable matter, bones meat scraps, paper and the like are softened and partially hydrolyzed.

The contents of the chamber 11 are dumped onto the conveyor generally indicated by the numeral 18 where they are transported for further processing and separation into useful glass, ferrous and non-ferrous materials as is known in the art. This may be accomplished by sorting line conveyor system that utilizes either manual or mechanical separation techniques or a combination of these techniques well known in the art.

EXAMPLE

About 6 tons of municipal solid waste was placed into rotatable chamber 11. Chamber 11 had a diameter of about 8 feet and a length of about 40 feet. Perforated drum 16 had a diameter of 6 feet and a length of about 40 feet. The chamber 11 was rotating when the municipal solid waste was added to chamber 11. Saturated steam was injected into chamber 11 continuously until the temperature inside the chamber reached about 212 degrees F. The chamber was then rotated for about 30 minutes at 6 rpm to agitate the contents.

The contents were removed from chamber 11 and sifted through a screen to separate the inorganic fraction from the organic fraction. The inorganic fraction was found to have a moisture content ranging from about 35% to about 70%.

The resulting organic pulp had the following properties:

1. All screened organic particles were less than 1.25 inches in diameter.
2. Nitrogen content was about 1%.
3. The screened organic pulp was suitable for use as a compost, soil additive, or combustion fuel.
4. Color and texture was uniform.
5. The pulp was suitable for chemical and biological conversion to other fuels and chemicals.

Rotatable chamber 11 can be operated continuously by adding solid waste material to the entrance 10 while rotating chamber 11 while continuously heating the interior of chamber 11 by steam or hot air injection.

Although the preferred embodiments of the present invention have been disclosed and described in detail above, it should be understood that the invention is in no sense limited thereby, and its scope is to be determined by that of the following claims:

What is claimed is:

1. A method for treating solid municipal waste material containing inorganic and organic waste comprising:
    a. feeding said waste material into a rotatable chamber having a first end for receiving said waste material and a second end for discharging waste material from said rotatable chamber, said rotatable chamber being open to the atmosphere,
    b. adding water to said rotatable chamber,
    c. heating said waste material in said chamber from about 10 minutes to about 90 minutes while rotating said rotatable chamber by injecting steam at a temperature of from about 212 degrees F. to about 500 degrees F. into said rotatable chamber to heat said waste material to a temperature of from about 212 degrees F. to about 500 degrees F. to sterilize waste material and soften said organic waste material,
    d. conveying said waste material through said rotatable chamber and removing treated waste material from said rotatable chamber while said rotatable chamber is rotating and said steam is being injected, and
    e. separating a portion of said inorganic waste from said organic waste.

* * * * *